United States Patent
Salotra et al.

(10) Patent No.: US 6,855,522 B2
(45) Date of Patent: *Feb. 15, 2005

(54) SPECIES-SPECIFIC PCR ASSAY FOR DETECTION OF *LEISHMANIA DONOVANI* IN CLINICAL SAMPLES OF KALA-AZAR AND POST KALA-AZAR DERMAL LEISHMANIASIS

(75) Inventors: Poonam Salotra, New Delhi (IN); Gannavaran Sreenivas, New Delhi (IN); Gregory P. Pogue, Vacaville, CA (US); Hiralal Nakhasi, Potomac, MD (US)

(73) Assignee: Indian Council of Medical Research, New Delhi (IN)

( * ) Notice: Subject to any disclaimer, the term of this patent is extended or adjusted under 35 U.S.C. 154(b) by 0 days.

This patent is subject to a terminal disclaimer.

(21) Appl. No.: 10/086,184

(22) Filed: Feb. 27, 2002

(65) Prior Publication Data

US 2003/0162182 A1 Aug. 28, 2003

(51) Int. Cl.$^7$ ............................ C12P 19/34; C12Q 1/68; C07H 21/04

(52) U.S. Cl. ........................ 435/91.2; 435/91.1; 435/6; 536/23.1; 536/24.3; 536/24.33

(58) Field of Search ................................ 435/91.2, 91.1, 435/6, 810; 536/23.1, 24.3, 24.33

(56) References Cited

U.S. PATENT DOCUMENTS 4,918,166 A * 4/1990 Kingsman et al. .......... 530/350
6,469,152 B2 * 10/2002 Gaines et al. .................. 536/23

* cited by examiner

Primary Examiner—Kenneth R. Horlick
Assistant Examiner—Cynthia Wilder
(74) Attorney, Agent, or Firm—Ladas & Parry

(57) ABSTRACT

The present invention relates to a polymerase chain reaction (PCR) assay for the diagnosis of leishmaniasis using specific oligonucleotide primers for the identification of *Leishmania donovani* parasites in clinical samples.

9 Claims, 6 Drawing Sheets

Figure 1:
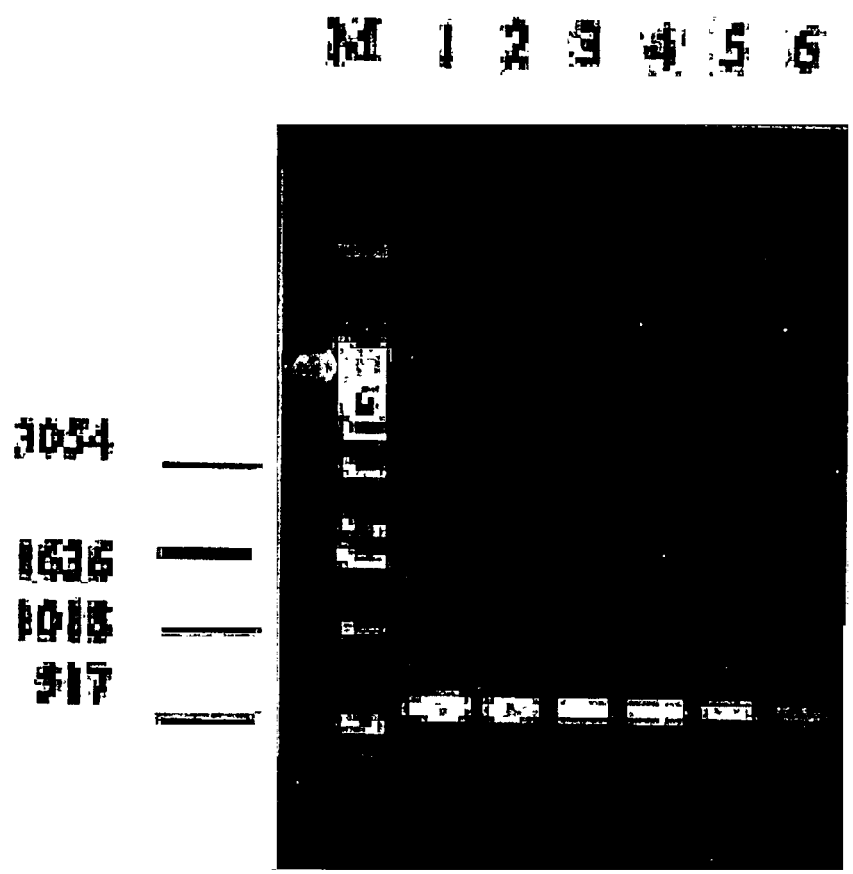

```
  1 gaattcgccg aaaaatgacc gaaaatgggc caaaaaccca aactttctg gtcctccggg
 61 taggggcgtt ctgcgaaaac cgaaaaatgg gtgcagaaat cccgttcaaa aaatagccaa
121 aaatgccaaa aatcggctcc gaggcgggaa actgggggtt ggtgtaaaat agggtcgggt
181 ggaggggaaa ttcggggctc ggacgtgtgt ggatatggcc tgggtgggga ctttggagtg
241 ggttgtactt gtatggggtt ttggacctgg cttggggttt gggggttggt gtgggaaagg
301 ggttggcgct atttggagtg acgttggctc ttttgataat tgatattgt tttaaactgg
361 attggttcgg ctggatatac gttggttggg ttggatttgg attggatttg gattttgtac
421 ggggtttggag gcttgatttg gggttgagga gtttgtgggg atagtttggg atgttagtat
481 ggaatgtagc ttcctttaat ataaatatta gttggggctg ttgcattagt ttgttccacg
541 ggagtagcct caggactta ggcgggagat actatattat cggtagtata atatcataag
601 tatacggtat agatatatgt taattgtagt atattgtaga tctatgttac agtgtatagt
661 ctatgaactt actagatata atttgtattt gatgctatag tgctactgat agagtgtacc
721 tatcactagt atagacgtag ctgaagctcc ttaaatgggt gggaatgggt gtgagggctg
781 gaagagacac tg
```

FIG. 6

SPECIES-SPECIFIC PCR ASSAY FOR DETECTION OF *LEISHMANIA DONOVANI* IN CLINICAL SAMPLES OF KALA-AZAR AND POST KALA-AZAR DERMAL LEISHMANIASIS

FIELD OF THE INVENTION

The present invention generally relates to a polymerase chain reaction (PCR) assay for the diagnosis of leishmaniasis. More particularly, the invention provides specific oligonucleotide primers for the identification of *Leishmania donovani* parasites in clinical samples. Furthermore, the invention also provides methods for detection of leishmaniasis using the said primers.

BACKGROUND OF THE INVENTION

The protozoan parasites of the genus Leishmania are the causative agents of visceral leishmaniasis (VL), also called kala-azar (KA). KA is a symptomatic infection of the liver, spleen and bone marrow caused by organisms of *Leishmania donovani* complex. The annual incidence and prevalence of cases of visceral leishmaniasis worldwide is 0.5 million and 2.5 million respectively. Of these 90% of cases occur in India, Nepal, Bangladesh and Sudan. The causative organism in the Indian subcontinent and Africa is *L. d. donovani*, while in the Mediterranean basin and South America it is *L. d. infantum*.

PKDL (Post kala-azar dermal leishmaniasis) is an unusual dermatosis that develops as a sequel of KA, producing gross cutaneous lesions in the form of hypopigmented macules, erythema and nodules. The disease is relatively common in the Indian subcontinent and less frequent in East Africa, but exceptional in the American and European continents. Detection and characterization of Leishmania from patients of both KA and PKDL is important for deciding treatment regimens as well as for understanding the disease epidemiology.

Current diagnostic methods based on parasite detection (stained smears, culture and histopathology) and immunological methods (DAT, ELISA etc.) have several limitations including low sensitivity and specificity. Procedures for demonstration of the parasite in spleen or bone marrow in KA and in skin lesions in PKDL are invasive and often not sensitive enough. Immunological methods fail to distinguish between past and present infections and are not reliable in case of immuno-compromised patients. Furthermore, both of these methods do not address the problem of species identification, which is important to determine appropriate treatment regimens and designing control measures. Procedures involving the use of monoclonal antibodies, isoenzyme and schizodeme analysis and DNA hybridization have to be resorted to. Most of these procedures are tedious and require massive cultures of parasites. There is, therefore, an urgent need to develop diagnostic procedures that are simple, sensitive and specific.

In recent years PCR based diagnostic methods have been described for leishmaniasis, with a wide range of sensitivity and specificity. An excellent target for a sensitive and rapid detection method is the kinetoplast mini-circle DNA, which are present at thousands of copies per cell. The mini-circles have been used as targets for selective amplification of parasite DNA in various studies Aviles, H., A. Belli, R. Armijos, F. P. Monroy, and E. Harris J. Parasitol. 1999, 85:181–187; BhattacharyaR., K. Das, S. Sen, S. Roy, and H. K. Majumder. 1996. Microbiol. Lett. 135:195–200; Nuzum, E., F. White III, C. Thakur, R. Dietze, J. Wages, M. Grogi, and J. Berman. 1995 J. Lnf. Dis. 171: 751–754; Rogers M. R, Popper S. J., and Wirth D. F. 1990. Exp. Parasitol. 71: 267–275; Smyth, A. J., A. Ghosh, Md. Q. Hassan, D. Basu, M. H. L. De Bruijn, S. Adhya K. K. Mallik, andD. C. darker. 1992, Parasitol 105: 183–192.

Wirth and Pratt (Proc Natl Acad Sci USA. 79:6999–7003 (1982) have described a hybridization assay for the detection of Leishmania parasites using probes to parasite kinetoplast DNA. This assay detects parasites in cutaneous lesions at a sensitivity level of 1,000–10,000 parasites per biopsy specimen. The specimens are collected by touch-blotting of nitrocellulose sheets over a small area of infected skin. However, this method is not sensitive enough to detect small numbers of parasites and relies on probes that have to be purified from the parasites themselves. This requires growth of these organisms in large quantities in the laboratory.

A more sensitive assay has been sought for Leishmania parasites which will be sensitive, specific, and thus be useful in early diagnosis of infection, will identify the species of parasites more likely to induce severe disease, and aid evaluation of chemotherapy and screening of blood bank samples.

To this end, the Applicant has exploited the kinetoplast mini-circle DNA present in leishmania parasites and used these kinetoplast sequences to develop novel oligonucleotide primers which are extremely sensitive and capable of detecting leishmanial parasites from the peripheral blood and skin lesions of infected patients.

OBJECTS OF THE INVENTION

The main object of the invention is to provide novel species specific and highly sensitive oligonucleotide primers for detection of leishmanial parasites in clinical samples of patients.

Another object of the invention is to provide oligonucleotide primers which are useful for identification of *L. donovani* parasite DNA from peripheral blood of KA patients and skin lesions of PKDL patients.

Yet another object of the invention is to provide a method for detection of leishmanial parasites in clinical samples obtained from patients.

Still another object is to provide an assay which is highly species specific and sensitive for the detection of leishmanial DNA in clinical samples.

SUMMARY OF THE INVENTION

The invention provides a method for detection of leishmanial parasites in clinical samples using novel oligonucleotide primers which are species specific and highly sensitive to DNA of *L. donovani* parasites.

DESCRIPTION OF THE ACCOMPANYING DRAWINGS

FIG. 1. Sensitivity of the PCR assay. PCR amplification of the serially diluted *L. donovani* (DD8) DNA analyzed on agarose gels. DNA was extracted from parasite cultures and amplified as described in materials and methods. Lane: M, 1 kb Ladder (Gibco BRL); lane1, 10 ng DNA; lane 2, 1 ng; lane 3, 10 pg; lane 4, 1 pg; lane 5, 10 fg; lane 6,1 fg.

Figure 2:
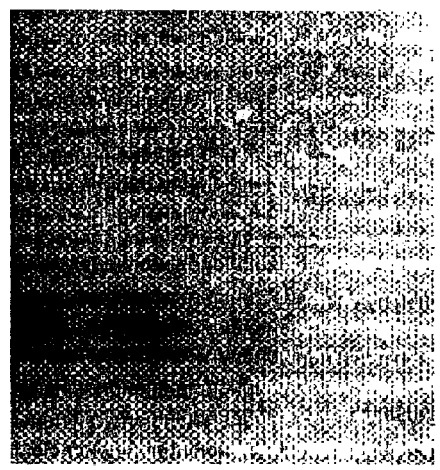

FIG. 2. Sensitivity of PCR amplification of Leishmania kDNA followed by southern blot analysis. PCR reaction contained 100 ng of human genomic DNA and the indicated amount of total DNA from *L. donovani* DD8. The PCR product was probed with parasite kDNA and exposed for about one hour. Lane 4 represents PCR reaction containing only human DNA as a control.

Figure 3:
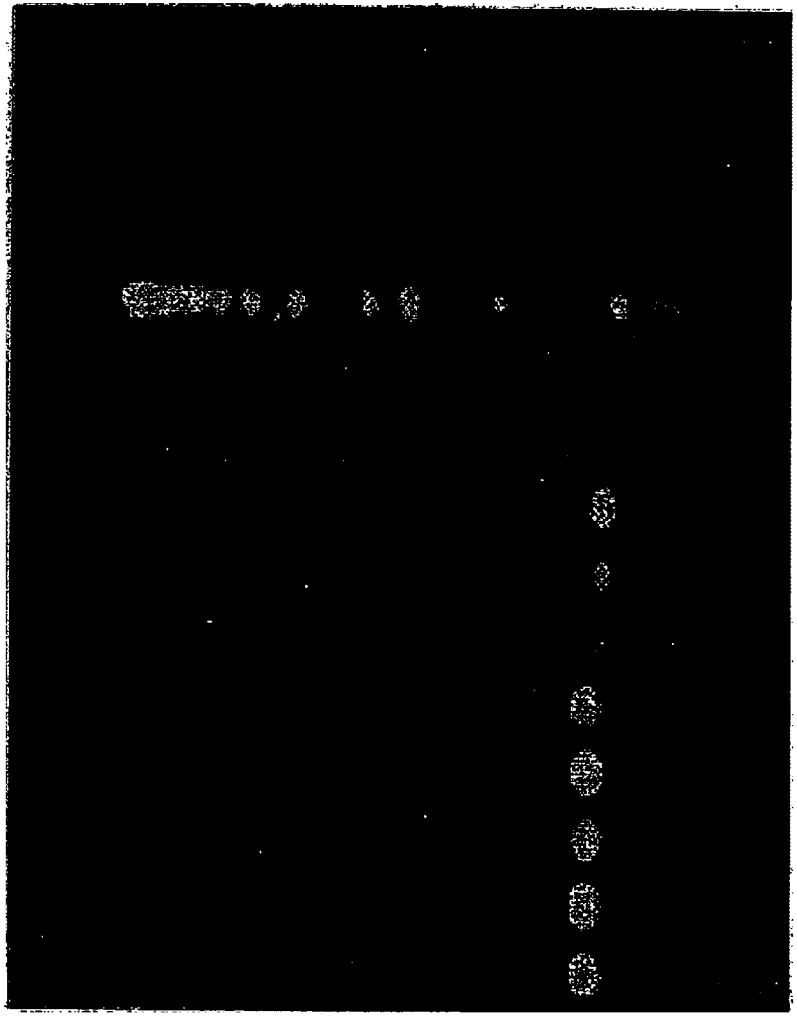

FIG. 3. Amplification of parasite DNA from various strains and isolates of Leishmania. 1 ng of DNA isolated from parasite cultures was subjected to PCR and analyzed. Lane 1, *L. donovani* AG83; lane 2, *L. donovani* DD8;lane 3, *L. donovani* IICB8;lane 4, *L. donovani* IICB6; lane 5, *L. donovani* IICB 7 (PKDL origin); lane 6, *L. donovani* 1S; lane 7, *L. donovani* WR684; lane 8 *L. donovani* infantum; lane 9, *L. tropica* WR683; lane 10, *L. major* LV 39, lane M, 1 kb ladder; lane 11, Plasmodium; lane 12, *M. leprae*; lane 13, *M. tuberculosis*.

Figure 4:
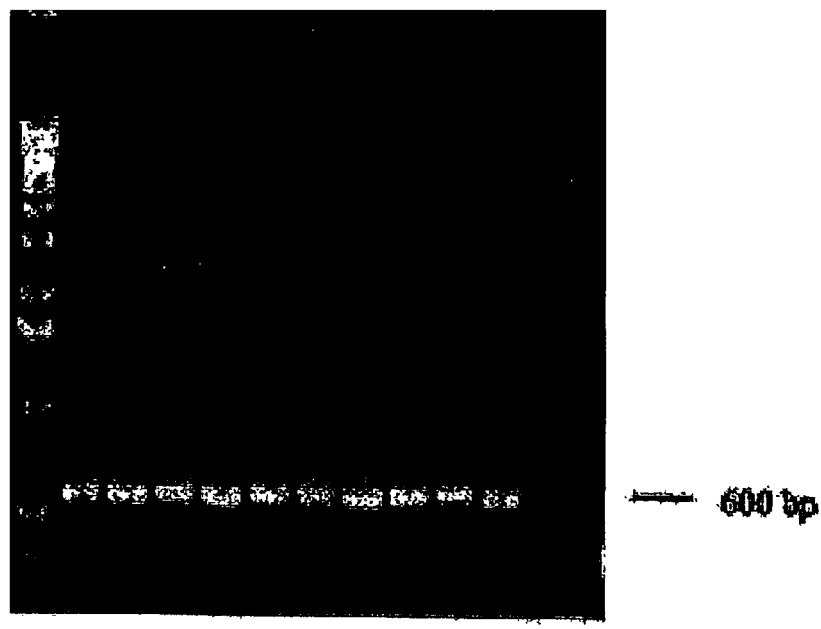

FIG. 4. DNA amplification from recent field isolates of KA and PKDL. 1 ng DNA extracted from culture of parasite isolates were used for PCR amplification. Lanes M, 1 kb ladder; 1,KA-1; 2,KA-2; 3, KA-3; 4, KA-4; 5, KA-5; 6, PK-1; 7,PK-2; 8, PK-3; 9, PK-4; 10, PK-5; 11, Isolate from a cutaneous leishmaniasis case.

Figure 5:
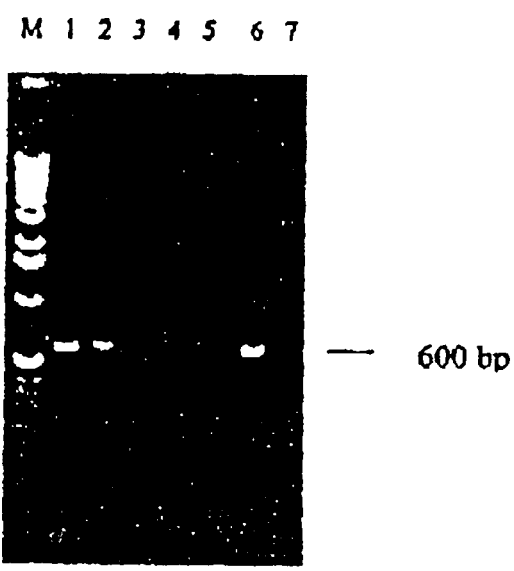

FIG. 5. PCR assay with clinical samples of KA and PKDL. 100 ng of DNA isolated from clinical samples was used for PCR amplification. Lanes M, 1 kb ladder; lane 1, KA Bone marrow; lane 2, KA Blood; lane 3, Malaria Blood; lane 4, Tuberculosis blood; lane 5;Blood from endemic control; lane 6, PKDL skin lesion; lane 7, Leprosy lesion.

FIG. 6 Sequence of PCR product (SEQ. ID. NO: 3) with DNA isolated from L. donovani DD8 strain, isolates and clinical samples of KA and PKDL. PCR products obtained with DNA isolated from *L. donovani* DD8 strain, parasite isolates from KA and PKDL patients (2 each) and clinical samples (2 each of KA blood and PKDL tissue) were subjected to sequence analysis. Identical sequence of PCR produt was obtained in each case, which matched exactly with the published sequence of a 792 bp kDNA minicircle segment of DD8' strain of *L. donovani* (GenBank accession no. Y11401). Position of primers is indicated in bold.

DETAILED DESCRIPTION OF THE INVENTION

Accordingly, the invention provides novel oligonucleotide primers which are useful for the detection of leishmanial parasites in clinical samples. The primers are species specific and in the present case, specific to *Leishmania donovani*.

The primers developed are 5'-AAATCGGCTCCGAGOCGGGAAAC-3' and 5'-GGTACACTCTATCAGTAGOAC-3' both together designated as Ld1 primers or SEQ ID NOS: 1 and 2 respectively. These primers have been developed after analysis of the 792 bp *L. donovani* kinetoplast minicircle sequence deposited at www.ncib.nlm.nih/gov/genbank at Accession No. Y11401. The web site provides more than 245 entries for leishmanial kDNA, all of which have been analyzed by this Applicant. It is after such detailed analysis that the primers of the invention were developed.

The primers identified in the present invention have been characterised from the 792 bp *L. donovani* kinetoplast minicircle sequence deposited at vww.ncib.nlm.nih/gov/genbank at Accession No. Y11401. The primers can be artificially synthesized by any person having average skill in the art by using conventional techniques and instruments such as Applied Biosystems DNA/RNA synthesizer model 394.

In the present invention, the primers were synthesized as described above using the said Applied Biosystems DNA/RNA synthesizer model 394. The DNA from the clinical samples was amplified using the primers of the invention i.e. SEQ ID NO: 1 and SEQ ID NO: 2. The PCR products were analyzed by gel electrophoresis. The PCR products were subjected to southern blot analysis and hybridized with $^{32}$P labeled cloned *Leishmania donovani* kDNA fragment (kinetoplast DNA). The PCR products were cloned in an appropriate vector system, sequenced and analysed using PC-Gene software to arrive at the said novel primers.

Thus, the invention provides a PCR primer set specific for *Leishmania donovani*, said primer set being (1) a first pair of oligonucleotides having the sequences givers by SEQ ID NO: 1 and SEQ ID NO: 2 wherein the primer set is effective in a PCR assay for detecting the presence of *Leishmania donovani* infection in samples derived from patients infected by leishmaniasis. The primer set is a first pair of oligonucleotides. SEQ ID NO: 1 is 5'-AAATCGGCTCCGAGGCGGGAAAC-3' and SEQ ID NO: 2 is 5'-GGTACACTCTATCAGTAGCAC-3'.

Further, the invention provides a method of detecting the presence of Leishmania donovani in a sample from a patient suspected of leishmaniasis, said method comprising the steps of:

1) providing a sample from the patient suspected fo being infected with *Leishmania donovani*
2) isolating and purifying the nucleic acids from the sample,
3) forming a polymerase chain reaction solution containing at least a portion of nucleic acids form step (b), a PCR primer set consisting of SEQ ID NOS 1 and 2, a mixture of nucleoside triphosphate monomers, and an enzyme Taq polymerase in a buffered solution,
4) carrying out a polymerase chain reaction on the PCR reaction solution to amplify any *Leishmania donovani*-specific nucleic acid; and
5) analyzing the *Leishmania donovani*-specific nucleic acids obtained in the polymerase chain reaction using gel-electrophoresis method and staining the resulting gel, wherein the presence of a band at about 600 bp is indicative of the presence of *Leishmania donovani* parasites in the patient.

In this method, the sample is obtained from peripheral blood or skin lesions of the patient. The nucleic acids are treated with phenol chloroform and ethanol to isolate purify them. The primers of the invention are sensitive so as to detect even 10 fg Leishmania DNA diluted in 10 million fold excess of human DNA in PCR reactions. The PCR reaction is performed in a thermal cycler overlaid with mineral oil.

In the said method, the steps of amplifying the *Leishmania donovani*-specific nucleic acid comprises initial denaturation at 94° C. for 2 min followed by 40 cycles of denaturation at 94° C. for 1 min, annealing at 45° C. for 1 min and extension at 72° C. for 2 min, and a final extension at 72° C. is carried out for 3 min so that multiple copies of the *Leishmania donovani* specific nucleic acid are produced.

In addition, the invention provides a kit for detecting *Leishmania donovani* in a sample, comprising oligonucleotide primers, wherein the primers comprise SEQ ID NO: 1 and SEQ ID NO: 2, and wherein the primers hybridize to the said *Leishmania donovani*.

As said earlier, the objective of the invention is to define a set of PCR primers based on kDNA sequences, which allow a sensitive and specific detection of *L. donovani*. Towards this end, the Applicant analyzed kDNA mini circle sequences from *L. donovani* DD8 strain of Indian origin and designed oligonucleotide primers that showed lack of cross-reactivity with organisms phylogenetically or geographically related. The sensitivity and effectiveness of the PCR-based detection system was seen in its ability to amplify kDNA fragments from as little as 1 fg DNA of *L. donovani* (FIG. 1). When the amplification properties of PCR were combined with the specificity and sensitivity of Southern-based DNA hybridization, kDNA fragments could be detected by probes generated from the parasite kDNA sequences in PCR reactions containing as little as 10 fg of Leishmania DNA diluted in 10 million fold excess of human DNA (FIG. 2).

Initially, the primers were evaluated with various strains of Old World Leishmania. Both strains of *L. donovani* of Indian origin, (i.e. DD8 and AG83) gave positive result in PCR, as did the three isolates from Indian patients (FIG. 3, lanes 1–5). These three isolates of *L. donovani* were isolated six years back from patients of KA and PKDL and preserved in the Parasite Bank at IICB, Calcutta by Dr. Dwijen Sarkar. Strains of *L. donovani* from Sudan and Ethiopia as well as *L. donovani* infantum from Spain reacted positive in PCR, though the bands were of significantly lower intensity (FIG. 3, lanes 6–8). DNA from *L. major* and *L. tropica* was not amplified indicating the species-specificity of primers (lanes 9 and 10). Species-specificity for *L. donovani* was further established, since the use of DNA up to long from three different strains of *L. major* and two strains of *L. tropica* described in materials and methods did not give any amplification. Specificity of the primers was also evaluated using DNA (10 ng) from microorganisms causative of the common infectious diseases prevalent in India such as Plasmodium, *Mycobacterium leprae*, *Mycobacterium tuberculosis*, there was no amplification with DNA from any of these organisms using the primers of the invention. (FIG. 3, lanes 11–13).

In order to establish the clinical utility of the assay, PCR amplification was evaluated with DNA from several recent isolates of the parasite. Parasite cultures were set up from bone marrow aspirates of five KA patients that reported to SJH over last two years (designated KA1–KA5). DNA isolated from each of these cultures was observed to be amplified in PCR assay (FIG. 4, lanes 1–5). The assay was also positive with a number of cultures isolated from dermal lesions of PKDL patients (PK1 to PK5) (FIG. 4, lanes 6–10) while the parasite culture isolated from a patient of cutaneous leishmaniasis hailing from Afghanistan gave no amplification in the PCR test (FIG. 4, lane 11). Sensitivity of the assay with the isolates of KA and PKDL was found to be 1 fg of total DNA.

A clinical study was undertaken with Indian patients of both KA and PKDL using PCR based on Ld I primers. The PCR assay was evaluated with clinical samples from KA and PKDL patients along with suitable controls. PCR analysis of representative sample from each of test materials i.e., bone marrow and whole blood from KA patients, blood from malaria and tuberculosis patients, blood from endemic controls, skin lesion from PKDL and leprosy patients is shown in FIG. 5. Only samples from bone marrow and blood from KA patients and from PKDL skin lesion were PCR positive (FIG. 5, lanes 1,2 and 6). Rest of the samples were negative (FIG. 5, lanes 3–5, and 7). All eight samples of bone marrow aspirates of Kala-azar patients gave positive result when subjected to PCR amplification (Table 1). The results showed that the primers could specifically amplify DNA from peripheral blood of 49/51 KA patients (Table 1). Identical results were obtained in PCR using DNA extracted by phenol chloroform method or QIAamp DNA blood minikit, indicating that either method could be employed. DNA from just 0.2 ml of patient's blood was found to be sufficient for the PCR test indicating tremendous clinical usefulness of the test. All malaria (15 cases) and tuberculosis (15 cases) blood samples were negative while two of the 20 endemic controls reacted positive in PCR (Table 1). A large majority of PKDL cases (45/48) gave positive result while all the leprosy cases (32/32) were negative (Table 1). Samples of normal dermal tissue from unaffected parts of skin of PKDL patients (19 cases) were all negative (Table 1). Sequence analysis of the PCR product obtained with DNA from clinical samples (KA blood and PKDL tissue) as well as from parasite isolates of KA and PKDL revealed that the sequence of the products was identical to that obtained with the DD8 strain of *L. donovani* (FIG. 6).

TABLE 1

Results of PCR assay in KA and PKDL clinical samples and controls

| Source of DNA | Total cases | Positive cases | % Positive |
| --- | --- | --- | --- |
| KA bone marrow | 08 | 08 | 100 |
| KA blood | 51 | 49 | 96 |
| Malaria blood | 15 | 0 | 0 |
| TB blood | 15 | 0 | 0 |
| Endemic controls | 20 | 2 | 10 |
| PKDL lesions | 48 | 45 | 93.8 |
| Leprosy lesions | 32 | 0 | 0 |
| Normal tissue from PKDL | 19 | 0 | 0 |

The invention is described in detail hereafter and this description should not be construed as a limitation on the scope of the invention.

Patients: Fifty one Kala-azar patients hailing from Bihar (India) and reporting to Safdarjung hospital (SJH), New Delhi (India) were included in the study at the pretreatment stage. The patients presented with characteristic symptoms of KA such as fever, hepatosplenomegaly, anemia and leukopenia. Only those cases were taken where the diagnosis of KA was confirmed by demonstration of parasites in bone marrow aspirates. Blood was taken from all 51 patients. In addition, bone marrow samples were obtained from 8 of these patients. Clinical samples were also taken from a total of 48 PKDL patients that were originally from Bihar (India) and reported to the Dermatology Department of SJH during the period from 1996–2000. Forty five of these reported history of KA while the remaining three were not aware of it. The time elapsed after cure from KA in the 45 patients ranged from 1–15 years.

Clinical diagnosis in 36 cases was based on condition characterized by erythematous indurate areas, papulonodular and hypochromic macules in a bilateral distribution. The remaining 12 patients had a predominantly macular presentation, most of them being the subject of a recent study. Slit skin smears stained by Giemsa were positive in only 10 cases. Histopathological findings on skin biopsies were similar to those reported earlier. The dermis showed a diffuse infiltration by lymphocytes, histiocytes and plasma cells. All patients responded well to therapy with sodium antimony gluconate. The control group of patients comprised of confirmed cases of malaria, pulmonary tuberculosis and lepromatous leprosy from SJH. Twenty healthy volunteers living in endemic area (such as Muzaffarpur, Bihar of India) were also included in the control group.

Parasites: Ten WHO reference strains of Leishmania originating from distinct geographic locations were used in the study. These included *L. donovani* DD8 (MHOM/IN/80/DD8) from India, *L. donovani* AG83 (MHOM/IN/83/AG83) from India, *L. donovani* 1S (MHOM/SD/00/1S-C12D) from Sudan, *L. donovani* WR 684 (MHOM/ET/67/82) from Ethiopia, *L. donovani* infantum (MCAN/SP/00/XXX) from Spain, *L. tropica* WR 683 (MHOM/SU/58/OD) from Soviet Union, *L. tropica* WR 664 (MHQM/SU/74/K27) from Soviet Union, *L. major* WR662 (MHOM/IL/67/Zericho WWR662) from Israel, *L. major* LV39 (MRHO/SU/59/P/LV39) from Soviet Union and *L. major* ASKH (MHOM/SU/73/5ASKH) from Soviet Union. All these strains are deposited at Montpellier International Cryobank, France. Three isolates of *L. donovani* (MHOM/IN/94/IICB6, MHOM/IN/94/IICB7, and MHOM/IN/94/IICB8) were kindly provided by Dr. D. Sarkar, IICB, Calcutta, India. These strains were isolated from patients of VL (IICB6 and IICB8) and PKDL (IICB7) originating from Bihar, India and characterized as *L. donovani*. Ten parasite isolates were set up in culture in our laboratory over last two years from patients of VL and PKDL reporting to SJH. All parasite cultures were set up and propagated in Medium 199 supplemented with 25 mM-HEPES pH7.5 and 10% fetal calf serum. Parasites were harvested in late log phase, washed in phosphate buffered-saline prior to DNA isolation.

Sample collection and DNA isolation: Bone marrow and skin scrapings were collected in NET buffer (150 mM NaCl, 15 mM Tris-HCl pH 8.30, 1 mM EDTA). Blood was collected in heparinised tubes. Samples were transported to the laboratory at ambient temperature, except for blood collected in endemic area in which case they were brought on ice. Samples were transferred to 4° C. and generally processed on the same day. Blood (0.2 ml to 1 ml) was treated with RBC lysis buffer (114 mMSodium phosphate pH8.0, 1 mM $NH_4Cl$) and the buffycoat isolated. DNA from parasite cultures as well as from clinical samples (Skin scrapings, bone marrow or blood) was isolated by overnight lysis in NET buffer with 100 µg/ml of Proteinase-K and 1% SDS. DNA was extracted by phenol-chloroform extraction and ethanol precipitation. In a few samples DNA was isolated from 0.2 ml blood using QIAamp DNA blood minikit (QIAGEN) in order to determine if this method provided any advantage over the phenol chloroform method for DNA extraction.

Oligonucleotide primers: The 792 bp *L. donovani* kinetoplast minicircle sequence (Accession no. Y11401) was analyzed using PC-Gene software programme and appropriate primers were identified. The two primers used were 5'-AAATCGGCTCCGAGGCGGGAAAC-3' (SEQ ID No. 1) and 5'-GGTACACTCTATCAGTAGCAC-3' (SEQ ID No. 2), together designated as LdI primers. These were synthesized using an Applied Biosystems DNA/RNA synthesizer model 394. The LdI primers amplify a fragment of approximately 600 bp that is seen on the gels.

PCR amplification: DNA from cultured parasites (1 ng) and from clinical samples (100 ng) was taken for amplification using the LdI primers described above. Reaction mixture (50 µl) contained 10mM Tris-HCl, pH 8.3, 50 mM KCl, 1.5 mM $MgCl_2$, 200 µM of each deoxynucleoside triphosphate, 50 ng of each primer, and 1.25 units of Taq DNA polymerase (Gibco BRL). Each reaction was overlaid with mineral oil and amplification was performed in a thermalcycler (Perkin Elmer) programmed for 40 cycles of denaturation at 94° C. for 1 min, annealing at 45° C. for 1 min and extension at 72° C. for 2 min, preceded by an initial denaturation 2 min at 94° C. Final extension was for 3 min at 72° C. Products were analyzed by electrophoresis in 1% agarose gel containing 0,5 µg/ml ethidium bromide, in TAE buffer and photographed under Wv illumination.

Southern Blot analysis: PCR products were analyzed in 1% agarose gel and Southern blot analysis was done as described in Joshi M et al, Mol. Biochem. Parasitol, 1993, 58: 345–354. Southern blots were hybridized with $^{32}P$ labeled cloned *Leishmania donovani* kDNA fragment using the conditions described in Joshi M et al, Mol. Biochem. Parasitol, 1993, 58: 345–354.

Sequencing reaction: The PCR amplification products from culture isolates and clinical samples of KA and PKDL were cloned into pGEMT-Easy vector system (Promega). DNA sequence was performed with the ABI PRISM Dye Terminator Cycle sequencing kit and an ABI PRISM automated sequencer, Model 377 (Perkin Elmer, Warrington, Great Britain). Briefly, the sequencing reaction mixture contained terminator ready reaction mix, DNA template, primer and 5% DMSO (dimethylsulphoxide). DMSO was added to keep the DNA template denatured since Leishmania DNA has a high GC content. The PCR reaction was carried out in DNA Thermal cycler Model 480. The PCR reaction conditions were followed as per the Perkin-elmer analytical manual. Sequences were assembled and edited in the Sequencher software (Gene Codes Corporation, Ann Arbor, Mich.) and analyzed with Mac Vector DNA and protein sequence analysis software (Genetics Computer Group Inc., Madison, Wis.).

Observation: The PCR products amplified from the clinical samples of KA & PKDL showed identical nucleotide sequence as the cultured parasites. This confirmed presence of *Leishmania donovani* parasites in the sample.

Using the above method, the Applicant has developed a PCR assay that is species-specific for *L. donovani* kDNA among the Old World Leishmanias and can detect the parasite in a highly sensitive manner in clinical samples of Indian patients of both KA and PKDL. The assay could detect as little as I fg of parasite DNA from Indian strains of *L. donovani*, an amount that represents the equivalent of approximately 0.1 parasite. DNA from several parasite isolates obtained from patients of KA as well as PKDL originating from the endemic region in India was found to be amplified with equal sensitivity. Therefore the assay is theoretically capable of detecting a single parasite in a biological sample. The extreme sensitivity of the detection system was evident by its ability to amplify parasite DNA from peripheral blood of KA patients and dermal lesions of PKDL in a large majority of cases.

A total of 107 clinical samples from leishmaniasis patients were examined and 95% tested positive in PCR. The PCR described in this invention yielded a unique product of 600 bp and no non-specific side product or artifacts appeared on the gel. It has the advantage that results were easily and unequivocally interpreted upon analysis on agarose gels. The high level of sensitivity was reflected by the ability of the assay to detect parasite DNA in peripheral blood of KA patients, with 96% sensitivity in the 51 cases examined. Use of peripheral blood is advantageous because the collection procedure is less invasive and safer than the splenic or bone marrow biopsy specimen collection. In earlier studies for diagnosis of VL due to *L. donovani*, the sensitivity of PCR for blood samples has been found to be m the range of 45–94% based on smaller sample size ranging from 17 to 42. Adhya, S., M. Chatterjee, et al Trans. R. Soc. Trop. Med. Hyg. 1995: 89: 622–624, Andresen, K., S. Gasim, A. M. et al 1997,2: 440–444; Katakura, K., S. I. Kawazu, T. Naya, et al 1998. J. Clin. Microbiol. 36:2 173–2177; Nuzum, E., F. White III, et al. J. Inf. Dis. 171: 751–754; Osman, O. F., L. Oskam, et al J. Clin. Microbiol. 1977, 35:2454–2457; ++++ Singh N., M. D. Curran, et al Trop. Med & hit. Health. 1999, 4;448–453; Smyth, A. J., A. Ghosh, et al 1992. Parasitol 105: 183–192.

For detection of VL due to L. infantum, which may have a different pathogenesis, sensitivities between 64–97% have been reported with blood samples Lachaud, L., J. Dereure, et al 2000. J. Clin. Microbiol. 38:236–240; Mathis, A., and P. Deplazes. 1995. J. Gun. Microbiol, 33:1145–1149; Nuzum, E., F. White III, et al 1995. J. Inf. Dis. 171: 751–754. The sensitivity of detection was cent percent in the limited number of bone marrow samples that we examined. Bone marrow is known to have a high load of parasites while in peripheral blood the parasites are relatively scarce. Studies reporting PCR with detection sensitivity comparable to ours (less than a single parasite) did not obtain sensitivity as high as our assay when using blood samples of KA patients Katakura, et al 1998. Gun. Microbial. 36:2713–2177; Smyth, A. J., A. Ghosh et al 1992 Parasitol 105: 183–192.

With clinical samples the sensitivity in practice may be affected by factors such as accessibility of the DNA in parasite containing biopsy samples and the conditions used in the PCR amplifications.

DNA isolated from the pathogens causative of common co-endemic diseases (*M. leprae, M tuberculosis* and *Plasmodium*) was not amplified. Blood from malaria and tuberculosis patients were PCR negative in all cases (30/30) while two of the endemic controls were PCR positive, giving an overall specificity of 96% in the control blood samples examined. The two positive endemic controls were relatives of KA patients and possibly asymptomatic carriers since both cases reacted positive in ELISA with recombinant antigen k39 and in dipstick test using immunochromatographic strips coated with rk39 antigen (Salotra and Sreenivas, unpublished data), tests reported to be specific for KA. Singh, S., A. G. Sachs, et al 1995 J. Parasitol 81:1000–1003; Smyth, A. J., A. Ghosh, Ct al 1992. Parasitol 105: 183–192; Sundar, S., S. G. Reed, et al 1998. Lancet. 351:563–5651. A recent study has reported a PCR assay that could often detect parasitemia a few weeks before the appearance of any clinical signs or symptons Lachaud, L., J. Dereure, et al 2000. J. Clin. Microbiol. 38:236–240.

In India, 10–20 percent of patients apparently cured of KA develop PKDL. As there is no known animal reservoir in India, PKDL patients are considered an important source of transmission in recent epidemics of KA in India. The disease is easily confused with a number of skin disorders primarily leprosy due to similarities in the clinical presentation, therefore a high level of clinical expertise in needed to diagnose PKDL. Detection of LD bodies in skin lesions by microscopy gives positive result in only about 58% cases as parasites are scanty. Early recognition and treatment of PKDL would contribute significantly to the control of KA, as cases of PKDL constitute a reservoir for Leishmania parasite. The present assay validated in a large number of cases, provided a highly sensitive method for diagnosis of PKDL. The sensitivity of the assay was 93.8% for PKDL which is significantly higher than reported (82.7%) in a recent study with 32 PKDL patients in Sudan. Specificity of the test was 100% as all of the control tissues examined (32 leprosy lesions and 19 dermal samples from normal regions of the skin of PKDL patients) reacted negative.

Species-specificity of the assay was carefully evaluated taking DNA from different strains and species of Old World Leishmania. The assay was found to be positive with several WHO reference strains of *L. donovani* originating from distinct geographical regions. *L. donovani* from Ethiopia and Sudan and *L. d infantum* from Spain gave PCR products of identical size but of comparatively lower intensity probably due to lower copy number of the target KDNA sequence. Variations among *L. d. donovani* strains from different geographic regions have also been detected by RAPD-PCR and AP-PCR analysis. The primers were found to be species-specific for *L. donovani* as DNA from two other Leishmania species examined (*L. major* and *L. tropica*) was not amplified. One clinical isolate of *L. tropica* from a cutaneous leishmaniasis patient was also negative while several clinical isolates of KA and PKDL were all positive. The PCR products amplified from clinical samples of KA and PKDL showed identical nucleotide sequence as the cultured parasites.

The PCR provides a useful tool for simultaneous typing of parasites while the diagnosis is performed in clinical samples. Such a tool is necessary to complement diagnostic assays since most of them do not furnish the taxonomic information about theparasite required to determine the appropriate therapeutic regimens and control measures. Early detection and simultaneous typing would enable implementation of specific treatment to patients. Leishmania is increasingly recognized as an opportunistic pathogen during co-infection with HIV. Since incidence of HIV infection is on the increase in India, cases of co-infection with Leishmania are likely to present in future. In such cases immunological tests have particularly low sensitivity and the assay would provide a rapid detection as well as species identification of Leishmania.

Since this method is rapid and reproducible, the Applicant believes that it can be used for the reliable identification and characterization of cultured parasites. Another potential value of the test can be in detecting and typing parasites in vectors for epidemiological surveys and in retrospective studies of archival material.

The identification of conserved sequence elements represented within the kDNA of a given species of Leishmania would allow design of oligonucleotide primers to be used for species-specific identification of parasite in clinical samples. The Applicant has analyzed kDNA sequences from Old World Leishmanias and designed primers specific for *L. donovani* species to detect kDNA from a single parasite in presence of huge excess of human DNA. The utility of the primers designed for *L. donovani* has been examined in clinical samples from KA and PKDL patients in India. The PCR test was found to be sensitive enough to detect parasite DNA from peripheral blood of KA patients and from skin lesions of PKDL patients. Furthermore, the test was specific for *L. donovani* species of the parasite leading to simultaneous species identification of the parasite.

What is claimed is:

1. A PCR primer set specific for *Leishmania donovani*, said primer set comprising a pair of oligonucleotides having the sequences given by SEQ ID NO: 1 and SEQ ID NO: 2, wherein the primer set is effective in a PCR assay for detecting the presence of *Leishmania donovani* infection in samples derived from patients infected by leishmaniasis.

2. A PCR primer set as claimed in claim 1, wherein the primer set is consists of the pair of oligonucleotides.

3. A method of detecting the presence of *Leishmania donovani* in a sample from a patient suspected of being infected with leishmaniasis, said method comprising the steps of:
   a) providing a sample from the patient suspected of being infected with *Leishmania donovani*,
   b) isolating and purifying the nucleic acids from the sample,
   c) forming a polymerase chain reaction solution containing at least a portion of nucleic acids from step (b), a PCR primer set consisting of SEQ ID NO: 1 and SEQ ID NO: 2, a mixture of nucleoside triphosphate monomers, and an enzyme Taq polymerase in a buffered solution,
   d) carrying out a polymerase chain reaction on the PCR reaction solution to amplify any *Leishmania donovani*-specific nucleic acid; and
   e) analyzing the *Leishmania donovani*-specific nucleic acids obtained in the polymerase chain reaction using a gel-electrophoresis method and staining the resulting gel,
   wherein the presence of a band at about 600 bp is indicative of the presence of *Leishmania donovani* parasites in the patient.

4. A method as claimed in claim 3 wherein the sample is obtained from peripheral blood or skin lesions of the patient.

5. A method as claimed in claim 3 wherein the nucleic acids are treated with phenol chloroform and ethanol to isolate and purify them.

6. A method as claimed in claim 3 wherein the primers are sensitive so as to detect even 10 fg *Leishmania DNA* diluted in 10 million fold excess of human DNA in PCR reactions.

7. A method as claimed in claim 3 wherein the PCR reaction is performed in a thermal cycler overlaid with mineral oil.

8. A method as claimed in claim 3, wherein step d comprises amplifying the *Leishmania donovani*-specific nucleic acid by initial denaturation at 94° C. for 2 mm followed by 40 cycles of denaturation at 94° C. for 1 mm, annealing at 45° C. for 1 mm and extension at 72° C. for 2 mm, and wherein a final extension at 72° C. is carried out for 3 mm so that multiple copies of the *Leishmania donovani* specific nucleic acid are produced.

9. A kit for detecting *Leishmania donovani* in a sample, said kit comprising oligonucleotide primers, wherein the primers comprise SEQ ID NO: 1 and SEQ ID NO: 2, and wherein the primers specifically hybridize to the said *Leishmania donovani*.

* * * * *

UNITED STATES PATENT AND TRADEMARK OFFICE
CERTIFICATE OF CORRECTION

PATENT NO. : 6,855,522 B2
DATED : February 15, 2005
INVENTOR(S) : Poonam Salotra et al.

It is certified that error appears in the above-identified patent and that said Letters Patent is hereby corrected as shown below:

<u>Title page,</u>
Item [45], delete "*".
Item [*] Notice, delete "This patent is subject to a terminal disclaimer."

Signed and Sealed this

Twelfth Day of July, 2005

JON W. DUDAS
*Director of the United States Patent and Trademark Office*

SEQUENCE LISTING

```
<160> NUMBER OF SEQ ID NOS: 3

<210> SEQ ID NO 1
<211> LENGTH: 23
<212> TYPE: DNA
```

-continued

```
<213> ORGANISM: Artificial Sequence
<220> FEATURE:
<223> OTHER INFORMATION: Development of a species specific PCR assay
      for detection of Leis  hmania donovanni in clinical samples from
      patients with kala-azar and post-kala-azar dermal lesishmaniasis

<400> SEQUENCE: 1
aaatcggctc cgaggcggga aac                                              23

<210> SEQ ID NO 2
<211> LENGTH: 21
<212> TYPE: DNA
<213> ORGANISM: Artificial Sequence
<220> FEATURE:
<223> OTHER INFORMATION: Development of a species specific PCR assay
      for detection of Leis hmania donovanni in clinical samples from
      patentis with kala-azar and post-kala-azar dermal lesishmaniasis

<400> SEQUENCE: 2
gtgctactga tagagtgtac c                                                21

<210> SEQ ID NO 3
<211> LENGTH: 792
<212> TYPE: DNA
<213> ORGANISM: Artificial Sequence
<220> FEATURE:
<223> OTHER INFORMATION: Development of aspecies specific PcR assay
      for detection of Leish mania donovanni in clinical samples from
      patients with kala-azar and post-kala-azar dermal lesishmaniasis

<400> SEQUENCE: 3
gaattcgccg aaaaatgacc gaaaatgggc caaaaaccca aacttttctg gtcctccggg       60
tagggcgtt  cgtcgaaaac cgaaaaatgg gtgcagaaat cccgttcaaa aaatagccaa      120
aaatgccaaa aatcggctcc gaggcgggaa actgggggtt ggtgtaaaat agggtcgggt      180
ggaggggaaa ttcggggctc ggacgtgtgt ggatatggcc tgggtgggga ctttggagtg      240
ggttgtactt gtatggggtt ttggacctgg ctttggggttt ggggttggt gtgggaaagg     300
ggttggcgct atttggagtg acgttggctc ttttgataat tgatatttgt tttaaactgg      360
attggttcgg ctggatatac gttggttggg ttggatttgg attggatttg gattttgtac      420
ggggttggag gcttgatttg gggttgagga gtttgtgggg atagttttgg atgttagtat      480
ggaatgtagc ttcctttaat ataaatatta gttggggctg ttgcattagt ttgttccacg      540
ggagtagcct caggacttta ggcgggagat actatattat cggtagtata atatcataag     600
tatacggtat agatatatgt taattgtagt atattgtaga tctatgttac agtgtatagt      660
ctatgaactt actagatata atttgtattt gatgctatag tgctactgat agagtgtacc      720
tatcactagt atagacgtag ctgaagctcc ttaaatgggt gggaatgggt gtgagggctg      780
gaagagacac tg                                                         792
```